United States Patent
Antenucci et al.

(10) Patent No.: US 10,414,703 B2
(45) Date of Patent: Sep. 17, 2019

(54) PROCESSES FOR THE SYNTHESIS OF 1,2,3,4-TETRACHLORO-HEXAFLUORO-BUTANE

(71) Applicants: SOLVAY SPECIALTY POLYMERS ITALY S.P.A., Bollate, MI (US); RHODIA OPERATIONS, Paris (FR)

(72) Inventors: Emanuela Antenucci, Saronno (IT); Loïc Baussaron, Serpaize (FR); Stefano Millefanti, Tradate (IT); Vito Tortelli, Milan (IT); Francesco Venturini, Origgio (IT)

(73) Assignee: SOLVAY SPECIALTY POLYMERS ITALY S.P.A., Bollate (MI) (IT)

( * ) Notice: Subject to any disclaimer, the term of this patent is extended or adjusted under 35 U.S.C. 154(b) by 0 days.

(21) Appl. No.: 15/579,431

(22) PCT Filed: May 31, 2016

(86) PCT No.: PCT/EP2016/062235
§ 371 (c)(1),
(2) Date: Dec. 4, 2017

(87) PCT Pub. No.: WO2016/193248
PCT Pub. Date: Dec. 8, 2016

(65) Prior Publication Data
US 2018/0162793 A1 Jun. 14, 2018

(30) Foreign Application Priority Data
Jun. 4, 2015 (EP) ..................... 15305853

(51) Int. Cl.
*C07C 17/20* (2006.01)
*C07C 17/04* (2006.01)
(Continued)

(52) U.S. Cl.
CPC ........... *C07C 17/02* (2013.01); *B01J 19/0013* (2013.01); *B01J 19/0093* (2013.01); *C07C 17/04* (2013.01); *C07C 17/10* (2013.01); *C07C 17/204* (2013.01); *C07C 17/281* (2013.01); *C07C 19/10* (2013.01); *B01J 2219/00051* (2013.01)

(58) Field of Classification Search
None
See application file for complete search history.

(56) References Cited

U.S. PATENT DOCUMENTS 2,716,141 A 8/1955 Miller
8,536,387 B2 9/2013 Tortelli et al.
(Continued)

FOREIGN PATENT DOCUMENTS

CN 103664503 A * 3/2014
JP 2006342059 A * 12/2006 ............. C07C 17/10
(Continued)

OTHER PUBLICATIONS

Furuta, S. et al. Patent No. JP2006342059A, Published Mar. 3, 2005; pp. 1-18; English translation (Year: 2005).*
(Continued)

*Primary Examiner* — Medhanit W Bahta

(57) ABSTRACT

The present invention relates to processes for the manufacture of 1,2,3,4-tetrachloro-hexafluoro-butane in a microreactor.

7 Claims, 1 Drawing Sheet

(51) Int. Cl.
  *C07C 17/281* (2006.01)
  *C07C 19/10* (2006.01)
  *C07C 17/02* (2006.01)
  *C07C 17/10* (2006.01)
  *B01J 19/00* (2006.01)

(56) References Cited

U.S. PATENT DOCUMENTS

2009/0216053 A1 8/2009 Ohno et al.
2011/0071325 A1 3/2011 Ohno et al.
2013/0116483 A1 5/2013 Tortelli et al.

FOREIGN PATENT DOCUMENTS

WO 9922857 A1 5/1999
WO 2009087067 A1 7/2009

OTHER PUBLICATIONS

Tian, Y. et al. Patent No. CN103664503A, Published Mar. 26, 2014; pp. 1-6; English.*
Zhu, J. et al. "The research progress of hexafluorobutadiene synthesis" International Journal of Organic Chemistry, 2014, vol. 4, Issue: 5, pp. 331-338 (Year: 2014).*
Jähnisch et al. "Direct fluorination of toluene using elemental fluorine in gas/liquid microreactors" Journal of Fluorine Chemistry 105 (2000) 117-128 (Year: 2000).*
Miller, W.T. et al., "The mechanism of fluorination. III. Fluorine atom reactions. The olefin dimerization reaction", Journal of American Chemical Society, vol. 79, Jun. 20, 1957 (Jun. 20, 1957), pp. 3084-3089.

* cited by examiner

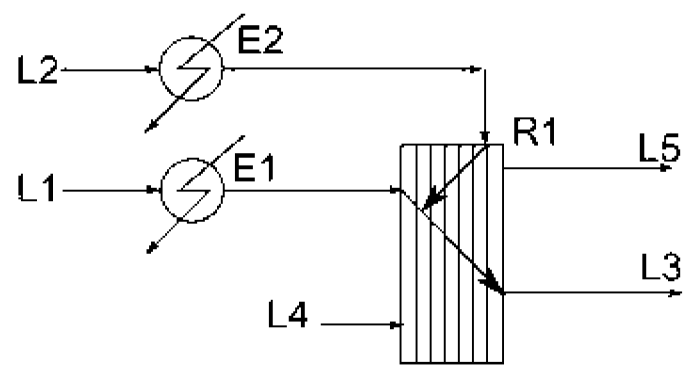

U.S. 10,414,703 B2

PROCESSES FOR THE SYNTHESIS OF 1,2,3,4-TETRACHLORO-HEXAFLUORO-BUTANE

CROSS REFERENCE TO RELATED APPLICATIONS

This application is a U.S. national stage entry under 35 U.S.C. § 371 of International Application No. PCT/EP2016/062235 filed May 31, 2016, which claims priority to European application No. 15305853.2 filed on Jun. 4, 2015. The entire contents of these applications are explicitly incorporated herein by this reference.

TECHNICAL FIELD

The present invention relates to processes for the manufacture of 1,2,3,4-tetrachloro-hexafluoro-butane in a microreactor.

BACKGROUND ART 1,2,3,4-tetrachloro-hexafluoro-butane (also known as "A316") is used as an intermediate compound in the synthesis of hexafluoro-1,3-butadiene (also known as "C4F6" or "HFBD"), a stable gas which is used in the semiconductor industry, in particular as etching gas for semiconductor fine processing.

Methods for the synthesis of hexafluoro-1,3-butadiene and its intermediate A316 have been already disclosed in the art.

US 2009/0216053 (SHOWA DENKO K.K.) discloses a process for producing hexafluoro-1,3-butadiene comprising (1) a step comprising allowing a compound having four carbon atoms each which bonds to an atom selected from the group consisting of a bromine atom, an iodine atom, and a chlorine atom, to react with a fluorine gas in the presence of a diluting gas in a gas phase, thereby preparing a mixture containing product (A), and (2) a step comprising eliminating halogens excluding a fluorine atom with a metal from the compound (A) prepared in step (1) in the presence of a solvent. The production process preferably comprises the step (1) of allowing 1,2,3,4-tetrachlorobutane to react with a fluorine gas in the presence of a diluting gas a gas phase thereby preparing a mixture containing 1,2,3,4-tetrachloro-hexafluoro-butane and a step (2) of dechlorinating 1,2,3,4-tetrachloro-hexafluoro-butane obtained in step (1) by a metal in the presence of a solvent.

Similarly, US 20110071325 (SHOWA DENKO K.K.) discloses a process for producing 1,2,3,4-tetrachloro-hexafluoro-butane, which comprises feeding fluorine gas to 1,2,3,4-tetrachlorobutane using plural reactors in the presence of a solvent and in the absence of a catalyst to allow the 1,2,3,4-tetrachloro-butane and the fluorine gas to react with each other, wherein a part or all unreacted fluorine gas discharged from one reactor is introduced into a reactor different from said one reactor.

U.S. Pat. No. 8,536,387 (SOLVAY SOLEXIS S.P.A.) discloses a process for preparing perfluoro-1,3-butadiene comprising the steps of (A) preparation of fluoro-halo-butanes of formula (V) $CF_2Y/$—$CFY//$—$CFY//$—$CF_2Y/$ in which Y/ and Y// identical or different may be H, Cl or Br, provided that they are not simultaneously H, starting with a chloroolefin having the formula (II) $CY"'Y=CY'Cl$ in which Y, Y' and Y" identical or different are H, Cl or Br, provided that they are not simultaneously H, and performing the following two steps: a fluorodimerization and a fluorination with elemental fluorine; and (B) dehalogenation or dehydrohalogenation of the fluoro-halo compounds of formula (V) to give the compound perfluoro-1,3-butadiene.

U.S. Pat. No. 2,716,141 (WILLIAM T. MILLER) 23 Aug. 1955 discloses a method for preparing aliphatic compounds completely substituted with chlorine and/or fluorine. More in particular, the method of preparing a perhalo butane comprises reacting at least one compound of formula $CR_1R_2=CR_3R_4$ with elemental fluorine at a temperature of less than 50° C., wherein each of R is selected from chlorine, fluorine, perfluoro acyclic groups and perfluorochloro acyclic groups.

Also, a general mechanism for the reaction of elemental fluorine with perhalo-olefins has been presented by MILLER, W. T., et al. The mechanism of fluorination. III. Fluorine atom reactions. The olefin dimerization reaction. *Journal of American Chemical Society*. Jun. 20, 1957, vol. 79, p. 3084-3089. The mechanism provides the formation of dimer addition products by the diffusion-controlled combination of free radicals which are produced in pairs with the intermediate formation of fluorine atoms.

WO 99/22857 (BRITISH NUCLEAR FUELS PLC) discloses a method of carrying out a chemical reaction between two fluids using a micro-reactor. Fluorination reactions are cited among a wide list of chemical reactions that are said that can be performed in a micro-reactor. However, first this patent application is silent about fluorodimerization reactions, which are known to be different from fluorination reaction. In addition, this patent application is silent about fluorination reactions starting from reagents bearing chlorine atoms. Indeed, it is known that this kind of reaction suffer from specific concerns. For example, it is known for example from MILLER, W. T., et al. The mechanism of fluorination. III. Fluorine atom reactions. The olefin dimerization reaction. *Journal of American Chemical Society*. Jun. 20, 1957, vol. 79, p. 3084-3089. that when chlorine-containing olefins varying amounts of by-products corresponding to substitution of chlorine by fluorine III and to the addition of chlorine by fluoride IV are usually formed.

SUMMARY OF INVENTION

The Applicant noted that despite 1,2,3,4-tetrachloro-hexafluoro-butane (A316) can be prepared by the methods known in the art, the productivity of the methods disclosed in the previous cited prior art documents was from about 1 $Kg/h*m^3$ to about 200 $Kg/h*m^3$.

However, as the demand of 1,2,3,4-tetrachloro-hexafluoro-butane (A316) is increasing in the semiconductor industry, the Applicant has now faced the problem to provide a method for manufacturing A316 with higher productivity when compared to the traditional methods, while keeping the costs of the industrial production as low as possible.

In doing so, the Applicant was well aware that the reactions of fluorination and fluorodimerization take place in particularly harsh environments, because they require very high or very low temperatures and of corrosive reagents, such as fluorine and hydrogen fluoride. These harsh conditions are troubling when microreactors are used, as microchannels having typically a diameter of less than 1 mm may be corrode and hence clogged, which would result in the interruption of the process and would require additional maintenance to the microreactor.

The Applicant has surprisingly found that when the synthesis of 1,2,3,4-tetrachloro-hexafluoro-butane (A316) is performed in a microreactor, it is possible to obtain productivity significantly higher than the productivity obtained with the synthesis known in the art. More in particular, the productivity increases from hundreds of kilos to tons, despite the fact that the residence time is reduced of 104 times with respect to the synthesis known in the art.

In addition, the Applicant has found that the synthesis of 1,2,3,4-tetrachloro-hexafluoro-butane (A316) can be performed in a microreactor without corrosion and clogging of the microchannels occurred.

Thus, in a first aspect, the present invention relates to a process for the production of 1,2,3,4-tetrachloro-hexafluoro-butane, wherein said process is performed in a microreactor.

Advantageously, the process according to the present invention is safer than the traditional synthesis, as it is not likely to undergo to explosions.

BRIEF DESCRIPTION OF THE DRAWINGS

The FIGURE is a schematic representation of a microreactor.

DESCRIPTION OF EMBODIMENTS

As used within the present description and in the following claims:

the term "productivity" indicates the rate of speed at which a product can be obtained in a chemical reaction and, more in particular, it is used to indicate the amount, expressed for example in Kg or tons, of 1,2,3,4-tetrachloro-hexa fluoro-butane (A316) produced per hour and per cubic meter of the reactor or of the microreactor. Thus, the term "productivity" is different from the term "yield" indicates the amount of product obtained in a chemical reaction;

the expression "residence time" is intended to indicate the ratio between the reaction volume and the volumetric flow of the gas phase fed into the microreactor. When the process is performed in gas phase, the reactions take place in the gas phase and the reaction volume corresponds to the volume of the gas into the microreactor. When the process is performed in liquid/gas phase or in liquid phase, the reactions take place at the interface between the gas and the liquid phase and in the liquid phase, respectively, and in both cases the reaction volume corresponds to the volume of the liquid phase into the microreactor;

the term "microreactor" (also known as "microstructured reactors" or "microchannel reactors") is intended to mean a device in which chemical reactions take place in a confinement with typical cross sectional dimensions below 1 mm. Said confinements are typically microchannels (also referred to as fine "flow ducts"), which are channels with a cross sectional dimension below 1 mm.

Microreactors can be used for reactions in liquid phase only (in this case they are also referred to as "micromixers"), in gas phase only, and in liquid/gas phase.

With reference to the FIGURE, a microreactor (M1) comprises inlets (L1, L2) for the reactants in liquid and/or gas phase into the reaction channel (not showed in the FIGURE), at least one outlet (L3) for the withdrawal of the final product. If required, the microreactor (M1) also comprises at least one inlet (L4) and at least one outlet (L5) for a heat transfer medium and heat exchangers (E1, E2).

Typically, the reaction channel is connected to a reaction plate (not shown in the FIGURE) comprising at least one microchannel, which is typically longitudinal in arrangement. Preferably, the reaction plate comprises at least five microchannels, more preferably at least ten microchannels. Typically, a microreactor comprises up to 10,000 microchannels.

The microchannels are typically linked to one or more entrances and/or exits via manifold or header channels (not showed in the FIGURE). The microchannels may be linked, e.g., in series or in parallel or in other configurations.

The microchannel cross section may be rectangular, square, trapezoidal, circular, semi-circular, ellipsoidal, triangular, U-shaped or the like. In addition, the microchannels can contain wall extensions or inserts that modify the cross-sectional shape, such as fins, grooves, etc. The shape and/or size of the microchannel cross section may vary over its length. For example, the height or width may taper from a relatively large dimension to a relatively small dimension, or vice versa, over a portion or all of the length of the microchannel itself.

Preferably, the microchannels have at least one cross-sectional dimension of from 1 μm to 1000 μm, preferably from 5 μm to 800 μm and more preferably from 10 μm to 500 μm. In a preferred embodiment, said at least one cross-sectional dimension is the largest cross-sectional dimension or the diameter of the microchannels.

Preferably, said microchannels have a length of from 1 cm to about 10 meters, more preferably from 5 cm to about 5 meters, and even more preferably about 10 cm to about 3 meters.

The selection of microchannel dimensions and overall length can be made by the skilled person depending on the residence time desired for the reactants into the microreactor, the contact time between the multiphase components, and other parameters.

Typically, a microreactor has an extremely high surface to volume ratio and hence exhibits enhanced heat and mass transfer rates when compared to conventional reactors. Preferably, the surface to volume ratio of the microreactor is from 4,000 to 40,000 $m^2/m^3$.

Preferably, the microreactor besides inlet(s) and outlet(s) contains other microchannel process control aspects, such as valves, mixing means, separation means, flow re-redirection conduit lines, heat flux control means, such as heat exchange conduits, pump(s), chambers or microchannels, for the controlled removal or introduction of heat to or from the solution or fluid flowing through the microchannels. The microreactor may also contain process control elements, such as pressure, temperature and flow sensor elements.

The temperature of the microreactor can be controlled for example by using a heat transfer fluid. Depending on the reaction to be performed, the microreactor is preferably kept at a temperature of from −150° C. to +300° C., more preferably of from −110° C. to 200° C.

Preferably, the process according to the present invention is carried out in a continuous mode, i.e. by continuously feeding the reactants into the microreactor.

The microreactor can be exercised in co-current or in counter-current. Preferably, the microreactor is exercised in co-current, i.e. the reactants were flowed from the top inlet to the bottom outlet.

Very good results have been obtained using a falling film microreactor (FFMR) having a surface to volume ratio between 10000 and 30000 $m^2/m^3$ and operating in co-current. Typically, said falling film microreactors comprise at least one reaction plate comprising several microchannels arranged next to one another.

Preferably, the process according to the present invention comprises a step of fluorination or fluorodimerization of a haloalkane or a (per)haloolefin.

The prefix "halo" in the term "haloalkane" is intended to indicate that the alkane is substituted with at least one halogen atom, said halogen atom being selected from fluorine, chlorine, bromine and iodine, more preferably from chlorine and bromine, even more preferably chlorine.

The prefix "(per)" used between parenthesis in the term "(per)haloolefin" is intended to indicate that the olefin can be fully or partially halogenated.

Preferably, the process according to the present invention is carried out in gas phase, in liquid phase or in gas-liquid phase.

More preferably, said gas phase comprises at least one gas selected from fluorine, nitrogen, helium, argon, $CO_2$, $CF_4$, $C_2F_6$, $C_3F_8$.

More preferably, said liquid phase comprises at least one solvent selected from chlorofluorocarbons; perhaloalkanes such as 1,2,3,4-tetrachloro-hexafluoro-butane (A316); perhaloolefins such as 1,2,3,4-tetrachloro-1,4-difluoro-1,3-butadiene and 1,2-dichloro-difluoro-ethylene; perfluoropolyethers; perfluoroethers; and per-fluorotrialkyl amines.

Preferably, the fluorination step is carried out by reacting said haloalkane or said (per)haloolefin in the presence of a source of fluorine, such as hydrogen fluoride.

More preferably, said process comprises one of the following reactions:

[a] fluorination of 1,2,3,4-tetrachlorobutane, or
[b] fluorination of 1,2,3,4-tetrachloro-1,4-difluoro-1,3-butadiene, or
[c] fluorodimerization of 1,2-dichlorodifluoroethylene to give 1,2,3,4-tetrachloro-hexafluoro-butane.

Preferably, reaction [a] is performed in gas phase or in liquid/gas phase, wherein said gas phase and said liquid phase are as defined above. More preferably, said gas phase comprises fluorine in admixture with nitrogen or helium. More preferably, said liquid phase comprises 1,2,3,4-tetrachloro-hexafluoro-butane (A316)

Preferably, reaction [a] is performed in the presence of a source of fluorine, such as for example hydrogen fluorine.

Preferably, in reaction [a] the residence time ranges from 0.01 to 0.5 seconds.

Preferably, reaction [a] is performed by keeping the microreactor at a temperature of from 80° C. to 300° C., more preferably from 100° C. to 275° C.

Preferably, reaction [b] is performed in liquid/gas phase, as defined above. More preferably, said gas phase comprises a mixture of fluorine and helium. More preferably, said liquid phase comprises 1,2,3,4-tetrachloro-1,4-difluoro-1,3-butadiene.

Preferably, in reaction [b] the residence time ranges from 0.01 to 0.5 seconds.

Preferably, reaction [b] is performed by keeping the microreactor at a temperature of from −10° C. to +50° C., more preferably from 0° C. to 25° C.

Preferably, reaction [c] is performed in liquid/gas phase, as defined above. More preferably, said gas phase comprises a mixture of fluorine and helium. More preferably, said liquid phase comprises 1,2-dichlorodifluoroethylene.

Preferably, in reaction [c] the residence time ranges from 0.01 to 0.5 seconds.

Preferably, reaction [c] is performed by keeping the microreactor at a temperature of from −150° C. to 0° C., more preferably from −100° C. to −65° C. and even more preferably from −95° C. to −85° C.

Should the disclosure of any patents, patent applications and publications which are incorporated herein by reference conflict with the description of the present application to the extent that it may render a term unclear, the present description shall take precedence.

The invention will be herein after illustrated in greater detail by means of the Examples contained in the following Experimental Section; the Examples are merely illustrative and are by no means to be interpreted as limiting the scope of the invention.

Experimental Section

Materials and Methods 1,2,3,4-tetrachlorobutane ($ClCH_2$—$CHCl$—$CHCl$—$CH_2Cl$) was prepared by chlorination of 1,3-butadiene following the procedure described in US 2013/0116483 (SOLVAY SPECIALTY POLYMERS ITALY S.P.A.). 1,2,3,4-tetrachloro-1,4-difluoro-1,3-butadiene ($FClC$=$CCl$—$CCl$=$CFCl$) was prepared following the procedure described in U.S. Pat. No. 8,536,387 cited above. 1,2-dichlorodifluoroethene ($CFCl$=$CFCl$—also referred to as "A1112") was prepared following the procedure described in US 2013/0116483 cited above.

Trichlorofluoromethane ($CCl_3F$—also referred to as Freon® 11) was obtained by Chemos GmbH and used as received. 1,2,3,4-tetrachloro-hexafluoro-butane ($F_2ClC$—$CFCl$—$CFCl$—$CF_2Cl$) when used as diluent was prepared following the procedure described in US 2009/0216053 or in US 2011/0071325 cited above.

In the following examples, Falling Film Microreactor (FFMR) supplied by Institut für Mikrotechnik Mainz GmbH was used, having a surface to volume ratio of about 20000 $m^2/m^3$ and comprising five U-shaped trenches (each having a volume of about 80 microliters) and a sealed gas chamber located on the top of the trenches. The microreactor was exercised in co-current, i.e. the reactants were flowed from the top inlet to the bottom outlet. Also, the inlets of the microreactor were connected to gas feed line and to a liquid feed line. The microreactor was properly cooled or heated as disclosed in detail in the following examples using a heat transfer fluid. In addition, before entering the microreactor, both the gas and the liquid were properly cooled or heated using two heat exchangers. The exhaust coolant and the biphasic flow containing the products left the microreactor via two separate ports.

In examples 1 and 1C the residence time was calculated as the ratio between the reaction volume reported in Table 1 and the overall gas phase volumetric flow of all the reactants fed into the reactor. In example 2, 3, 4, 2C, 3C and 4C the residence time was calculated as the ratio between the reaction volume reported in Table 1 and the overall gas phase volumetric flow of fluorine and nitrogen.

Example 1 [Reaction a]

The microreactor, kept at about 250° C., was fed with 272 mmol/h of fluorine diluted in 2.23 mol/h of nitrogen, 1.3 mol/h of HF and 44 mmol/h of 1,2,3,4-tetrachlorobutane.

The reaction took place in gas phase. At the end of the reaction the resulting product was condensed in a liquid phase, which was then analysed.

The residence time of the reactants, the amount of final product A316, the productivity and the volume of the reaction are reported in Table 1 below.

Example 2 [Reaction a]

The microreactor, kept at about 120° C., was fed with 6 Nl/h of fluorine diluted (1:1) with nitrogen as the gas phase and 60 mmol/h of 1,2,3,4-tetrachloro-hexafluoro-butane as diluent, 50 mmol/h of HF and 20 mmol/h of 1,2,3,4-tetrachlorobutane as the liquid phase.

The reaction took place at the interface between the liquid and the gas phases. At the end of the reaction, the resulting product was obtained as a liquid phase, which was then analysed without further treatment.

The residence time of the reactants, the amount of final product A316, the productivity and the volume of the reaction are reported in Table 1 below.

Example 3 [Reaction b]

The microreactor, kept at about 10° C., was fed with 120 mmol/h of fluorine diluted with 33.5 mmol/h of helium and 41.2 mmol/h of 1,2,3,4-tetrachloro-1,4-difluoro-1,3-butadiene.

The reaction took place at the interface between the liquid and the gas phases. At the end of the reaction, the conversion of fluorine was found to be quantitative.

The residence time of the reactants, the amount of product A316, the productivity and the volume of the reaction are reported in Table 1 below.

Example 4 [Reaction c]

The microreactor was fed with 33.5 mmol/h of fluorine diluted in 569 mmol/h of helium and 263 mmol/h of 1,2-dichloro-difluoro-ethylene.

The liquid inlet temperature was −104° C. (span between −112° C. and −103° C.) and the gas inlet temperature was −107° C. (span between −110° C. and −106° C.). The temperature of the microreactor was kept between −87° C. and −95° C.

The reaction took place at the interface between the liquid and the gas phases. At the end of the reaction, the conversion of fluorine was found to be quantitative.

The residence time of the reactants, the amount of product A316, the productivity and the volume of the reaction are reported in Table 1 below.

Comparative Example 1C

Reaction [a] was performed in a standard reactor, following the procedure disclosed herein below.

A tubular reactor of 0.2 L, kept at 250° C., was continuously fed with 44 mmol/h of 1,2,3,4-tetrachlorobutane and 272 mmol/h of fluorine diluted in 2.23 mol/h of nitrogen and 1.34 mol/h of HF.

The residence time of the reactants, the amount of product A316, the productivity and the volume of the reaction are reported in Table 1 below.

Comparative Example 2C

Reaction [a] was performed in a standard reactor, following the procedure disclosed herein below.

A reactor, kept at about 35° C. under stirring and containing 20 g of HF, 380 g of 1,2,3,4-tetrachloro-hexafluoro-butane as diluent and 100 g of 1,2,3,4 tetrachloro-butane, was fed for 21 hours with a gaseous mixture containing 3 Nl/h of $F_2$ and 3 Nl/h of $N_2$.

The residence time of the reactants, the amount of product A316, the productivity and the volume of the reaction are reported in Table 1 below.

Comparative Example 3C

Reaction [b] was performed in a standard reactor, following the procedure disclosed in U.S. Pat. No. 8,536,387 and disclosed herein below.

A reactor, kept at about 10° C. under stirring and containing 50 ml of $CF_3OCFClCF_2Cl$, was fed for one hour with a gaseous mixture containing 2.7 Nl/h of $F_2$ and 0.75 Nl/h of $N_2$ and with 9.4 g/h of liquid 1,2,3,4-tetra chloro-1,4-difluoro-1,3-butadiene.

The residence time of the reactants, the amount of product A316, the productivity and the volume of the reaction are reported in Table 1 below.

Comparative Example 4C

Reaction [c] was performed in a standard reactor, following the procedure disclosed herein below.

The synthesis of 1,2,3,4-tetrachloro-hexafluoro-butane was performed following the method disclosed in Miller T. at al cited above.

A reactor having volume of 0.25 L, kept at about −75° C. under stirring, was loaded with 107 g of 1,2-dichlorodifluoroethene diluted in 165 g of Freon® 11 as solvent.

0.49 mol of fluorine diluted with 0.49 mol/h of nitrogen were bubbled into the mixture in the subsequent 7 hours.

The residence time of the reactants, the amount of product A316, the productivity and the volume of the reaction are reported in Table 1 below.

TABLE 1

| Example No. | Amount of A316 [in g/h] | Residence time [in s] | Productivity [in Kg/(h*m³)] | Reaction volume [in L] |
|---|---|---|---|---|
| 1 | 12.5 | 0.38 | 1357 | 0.0092 |
| 2 | 4.7 | 0.12 | 11746 | 0.0004 |
| 3 | 8.0 | 0.42 | 20053 | 0.0004 |
| 4 | 7.4 | 0.11 | 18706 | 0.0004 |
| 1C(*) | 12.5 | 8.3 | 62 | 0.200 |
| 2C(*) | 0.2 | 192 | 1 | 0.32 |
| 3C(*) | 8.0 | 35 | 241 | 0.033 |
| 4C(*) | 6.3 | 208 | 35 | 0.181 |

(*)comparative

The invention claimed is:

1. A process for the production of 1,2,3,4-tetrachloro-hexafluoro-butane, said process comprising one of the following reactions:
   [a] fluorination of 1,2,3,4-tetrachlorobutane, or
   [b] fluorination of 1,2,3,4-tetrachloro-1,4-difluoro-1,3-butadiene, or
   [c] fluorodimerization of 1,2-dichlorodifluoroethylene,
wherein said process comprising performing the reaction in a microreactor.

2. The process according to claim 1, wherein said process is carried out in gas phase, in liquid phase or in liquid/gas phase.

3. The process according to claim 2, wherein said gas phase or said liquid/gas phase comprises at least one gas selected from the group consisting of fluorine, nitrogen, helium, argon, $CO_2$, $CF_4$, $C_2F_6$, and $C_3F_8$.

4. The process according to claim 3, wherein said liquid phase or said liquid/gas phase comprises at least one solvent selected from the group consisting of chlorofluorocarbons; perhaloalkanes; perhaloolefins; perfluoropolyethers; perfluoroethers; and perfluorotrialkyl amines.

5. The process according to claim 1, wherein reaction [a] is performed by keeping the microreactor at a temperature of from 80° C. to 300° C.

6. The process according to claim 1, wherein reaction [b] is performed by keeping the microreactor at a temperature of from −10° C. to +50° C.

7. The process according to claim 1, wherein reaction [c] is performed by keeping the microreactor at a temperature of from −150° C. to 0° C.

* * * * *